United States Patent [19]

Siedband et al.

[11] Patent Number: 4,730,895
[45] Date of Patent: Mar. 15, 1988

[54] FIBER OPTIC LINE GENERATOR SUITABLE FOR USE WITH INCANDESCENT LIGHT SOURCE

[75] Inventors: Melvin P. Siedband, Madison, Wis.; Charles Lescrenier, 660 Crescent Ct., Wauwatosa, Wis. 53213

[73] Assignee: Charles Lescrenier, Wauwatosa, Wis.

[21] Appl. No.: 413,056

[22] Filed: Aug. 30, 1982

[51] Int. Cl.⁴ .............................................. G02B 6/04
[52] U.S. Cl. ................................................. 350/96.24
[58] Field of Search ..................................... 350/96.24

[56] References Cited

U.S. PATENT DOCUMENTS 4,352,550 10/1982 Uchida ............................. 350/96.24

Primary Examiner—William L. Sikes
Assistant Examiner—Robert E. Wise
Attorney, Agent, or Firm—Andrus, Sceales, Starke & Sawall

[57] ABSTRACT

Apparatus generating a line of light includes a light source, such as an incandescent lamp. A condensing lens is interposed between the lamp and the receiving end of an optical fiber cable for applying the light of the lamp to the cable. The discharge end of the optical fiber cable is flattened into a linear configuration, one or a few fibers thick. The discharge end of the optical fiber cable is coupled to a light beam projector containing a lens focusing and projecting a plane of light. The plane of light forms a line when applied to a patient or other object. A plurality of optical fiber cables and projectors may be coupled to the lamp to provide a pattern of lines.

17 Claims, 4 Drawing Figures

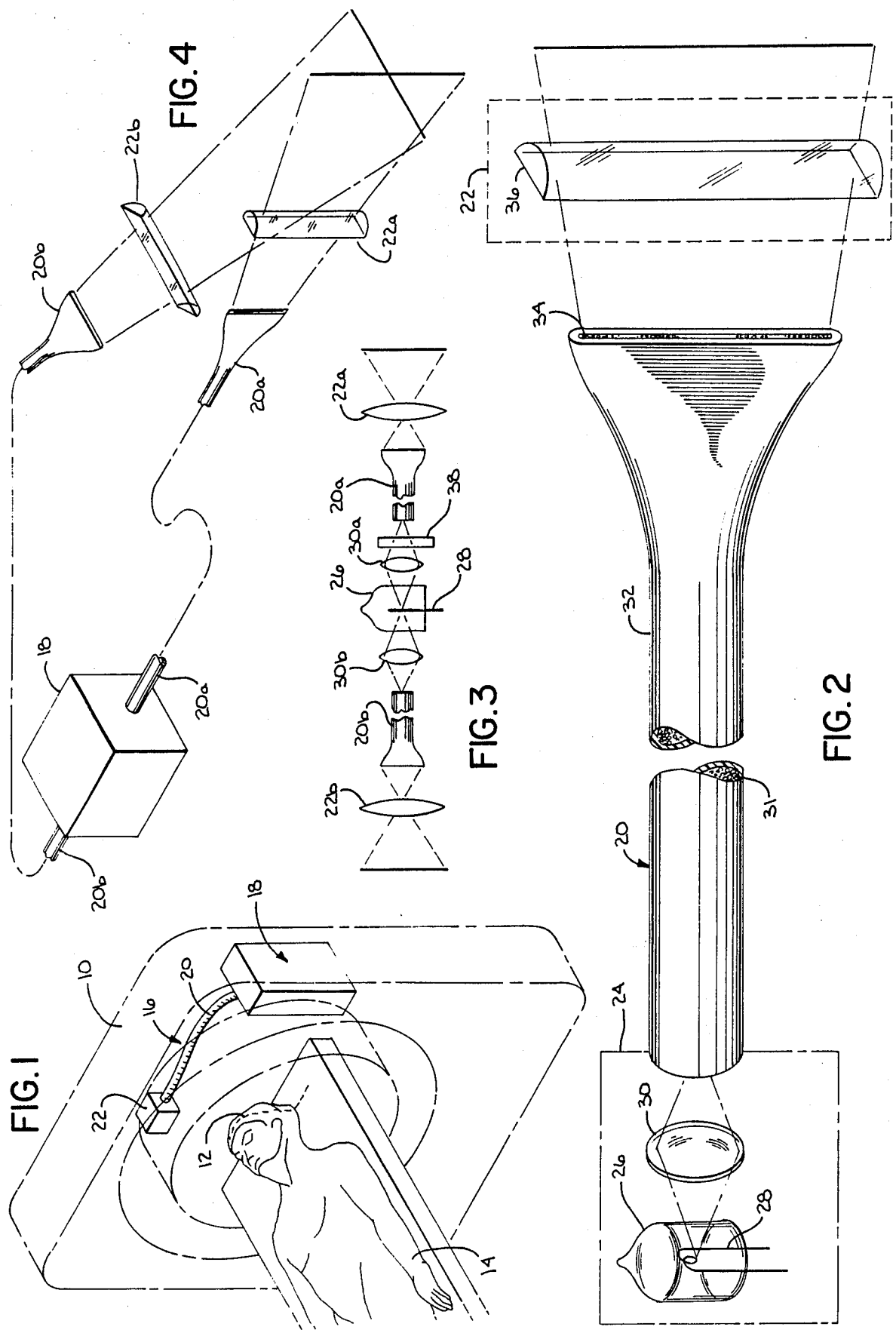

FIBER OPTIC LINE GENERATOR SUITABLE FOR USE WITH INCANDESCENT LIGHT SOURCE

X-ray equipment, such as that used for medical purposes usually requires some means for visually indicating the path of the X-ray beam, its exposure field, tomographic plane, or other properties. In many cases, lines of light are used for such purposes as, for example, a pair of crossed lines marking the axis of the X-ray beam or a rectangle of lines marking the field of the beam established by a collimator.

The visually observable lines may be provided by a laser light source feeding a lens, either directly or through an optical fiber coupling. See U.S. Pat. Nos. 4,011,403; 4,242,587; 4,255,657; and 4,337,502. Such line generators are highly satisfactory in forming lines of the desired brightness and narrowness. However, they require the expense of a laser and present a possible safety hazard to the eyes of patients or technicians.

Line generators using incandescent lights are also available. In their simplest form, these consist of an incandescent lamp and a slit in the lamp enclosure that forms the line. A condensing lens and/or cylindrical lens may also be used to assist in forming the line. Even with such assistance, the lines tend to have greater width and less brightness than required to adequately indicate the X-ray beam properties.

The brightness is rather low because the portion of the light of the lamp used to form the line is rather low and is spread over the entire area of the line. To obtain reasonable brightness with such a light source, the light must be extremely intense. This increases the thermal output of the lamp and limits its service life. Or, the size of the light bulb may have to be increased. In either event, operating disadvantages and inefficiencies appear in such a light source.

The object of the present invention is to provide an improved line generator. While not so limited, the invention finds particular utility with incandescent light sources and is capable of producing indicating lines of greater sharpness and brightness than those produced by conventional systems of this type while, at the same time, providing increased operating advantages and economies over such systems. The present invention also obviates the higher cost and possible safety hazards attendant the use of systems utilizing a laser light source.

Briefly, the apparatus of the present invention includes a light source such as an incandescent lamp. A condensing lens is interposed between the lamp and the receiving end of an optical fiber cable for applying the light of the lamp to the cable. The discharge end of the optical fiber cable is flattened into a linear configuration, one or a few fibers thick, for forming a line of light. The discharge end of the optical fiber cable is coupled to a light beam projector containing a lens focusing and projecting a plane of light. The plane of light forms a line when applied to a patient or other object. A plurality of optical fiber cables and projectors may be coupled to the lamp to provide a pattern of lines.

The invention will be further explained with the aid of the drawing in which:

FIG. 1 is a somewhat schematic perspective view of the line generator of the present invention in use with X-ray equipment;

FIG. 2 is a detailed schematic view of the line generator of the present invention;

FIG. 3 is a view similar to FIG. 4 showing the generation of a pair of light lines; and FIG. 4 is a perspective view of the apparatus of FIG. 3 showing use of a pair of light planes in generating a cross.

In FIG. 1, the numeral 10 indicates tomographic X-ray apparatus. It is desired to indicate the plane 12 of the tomographic image, for example, a brain scan, on patient 14. Light line generator 16 is employed for this purpose. Line generator 16 includes light source 18, optical fiber cable 20, and light line projector 22. Light line projector 22 is mounted on the X-ray apparatus so that the light is projected in the plane of the tomographic image and the light forms a corresponding indicating line 12 on patient 14 in apparatus 10. Light source 18 may be conveniently removed from projector 22 and the two connected by means of optical fiber cable 20.

FIG. 2 shows the details of light line generator 16. Light source 18 includes a source of light. As noted above, this light source may be of the incandescent type, such as a quartz-halogen lamp 26 and more particularly a quartz-iodine lamp having a flat filament configuration 28. Housing 24 also contains condensing lens or lenses 30 for concentrating the light of lamp 26 on the input end of optical fiber cable 20. Condensing lens 28 also shields cable 20 from the heat of lamp 26. The central plane of condensing lens 30 preferably lies parallel to the plane of the flat filament 28 so as to maximize the amount of light applied to lens 30.

Light source 18 may utilize a light source of the arc type or a laser, if desired.

Optical fiber cable 20 includes optical fiber means 31, preferably comprising a bundle of aligned optical fibers, surrounded by protective sheath 32. The input end of optical fiber cable 20 is connected to housing 24 by conventional coupling means, not shown. The entrance diameter of optical fiber means 20 on which the light of lamp 26 is focused by lens 30 will typically be round, although it may be optimally shaped to match the image of filament 28 of lamp 26, and of a magnitude not greater than the projected image of filament 28.

At the output end of fiber optic cable 20, optical fiber bundle 31 is flattened from the round condition into a line 34, one to several optical fibers in width, as shown in FIG. 2. The light emitted from cable 20 will thus be in the form of a plane that will form a line when applied to an object.

The output end of optical fiber cable 20 is coupled to projector 22. Projector 22 may contain lens 36 of the cylindrical type that forms and projects the image of the line 34 of the optical fibers toward patient 14 to generate line 12. The second end of optical fiber cable 20 is located at the focal point of the lens. Alternatively, a projection lens system of the imaging type such as a composite achromatic lens used in cinematic equipment, may be employed as lens 36. Inasmuch as a light line is being projected, such an imaging lens may be reduced to a rectangular section of the round lens.

Through the use of optical fiber cable 20 having a round or matched inlet end and a flat outlet end, the light coupling efficiency to light 26 through condensing lens 28 is kept high while the width of the light emitted from cable 20 is substantially reduced. This width may be 100 microns or less. In the case of an incandescent light source, substantial increases in image brightness over that of conventional incandescent lighting systems may thus be achieved along with greater bulb life and cooler operation.

FIG. 3 shows light bulb 26 providing light to a pair of fiber optic cables 20a and 20b and projectors 22a and 22b through condensing lenses 30a and 30b. FIG. 3 also diagrammatically shows use of a projection lens system of the imaging type. As further shown in FIG. 3, a colored filter 38 may be inserted in the light transmission path to color the resulting line for identification or other purposes.

FIG. 4 shows the apparatus of FIG. 3 used to provide a pair of crossed light lines indicating, for example, the center of an X-ray beam in conventional, non-tomographic, X-ray equipment. In a similar manner, four lines may be used to form a rectangle indicating the exposure field of an X-ray beam.

It will be appreciated that in instances in which it is desired to couple more than two fiber optic cables 20 to an incandescent light source, such as lamp 26, a vertical cylinder, a spherical, or another appropriate filament design may be utilized. Further, while the output end of optical fiber cable 20 is shown as a straight line 34 in FIG. 2, it may be a curved line or other appropriate configuration.

Various modes of carrying out the invention are contemplated as being within the scope of the following claims particularly pointing out and distinctly claiming the subject matter which is regarded as the invention.

We claim:

1. Apparatus for providing a line of light indicative of a property of an X-ray beam on an object comprising:
    an incandescent light source means providing a stationary beam of light;
    condensing lens means for focusing the light; and
    optical fiber means comprising an elongated solid bundle of aligned optical fibers having a first end light transmissively coupled to said light source means for receiving the focused light from said lens means, said first end of said optical fiber means having a diameter not greater than the image of said light source applied to said optical fiber means, said bundle of aligned optical fibers having a second end flattened to a width of at least one optical fiber for providing a plane of light forming the line of light indicative of the property of the X-ray beam when applied to the object.

2. The apparatus according to claim 1 wherein said light source means is of the quartz-halogen type.

3. The apparatus according to claim 2 wherein said light source means is of the quartz-iodine type.

4. The apparatus according to claim 1 wherein said incandescent light source means has an incandescent lamp.

5. The apparatus according to claim 4 wherein said lamp has a flat filament and wherein said light source means includes a condensing lens for focusing the light on said first end of said optical fiber means, the central plane of said condensing lens lying parallel to the plane of said flat filament.

6. The apparatus according to claim 4 wherein said incandescent lamp has a filament and wherein said bundle of optical fibers has a diameter at said first end not greater than the image of said filament applied to said optical fiber means.

7. The apparatus according to claim 4 wherein said incandescent lamp has a filament and wherein said bundle of optical fibers is shaped at said first end in accordance with the shape of said filament.

8. The apparatus according to claim 1 wherein said bundle of optical fibers is shaped at said first end in accordance with the shape of said light source.

9. The apparatus according to claim 1 further including a light beam projector light transmissively coupled to said second end of said optical fiber means for receiving the light from said second end for forming and projecting the line of light on the object.

10. The apparatus according to claim 9 wherein said light beam projector contains lens means for forming and projecting the line of light on the object.

11. The apparatus according to claim 10 wherein said lens means comprises a cylindrical lens.

12. The apparatus according to claim 10 wherein said lens means comprises at least a portion of an imaging lens means.

13. The apparatus according to claim 10 wherein said lens means comprises a rectangular section of a round composite achromatic lens.

14. The apparatus according to claim 1 wherein a plurality of optical fiber means are light transmissively coupled to said light source means for forming a plurality of lines of light.

15. The apparatus according to claim 14 wherein said plurality of lines of light are arranged in a predetermined pattern.

16. The apparatus according to claim 1 including means in the transmission path of the light for providing an identifying characteristic to the line of light.

17. The apparatus according to claim 16 wherein said identifying characteristic means is further defined as coloring the line of light.

* * * * *